United States Patent [19]

Podszun et al.

[11] 4,277,536

[45] Jul. 7, 1981

[54] BEAD POLYMERS OF VISCOUS DIMETHACRYLATES

[75] Inventors: Wolfgang Podszun, Cologne; Carlhans Süling, Odenthal; Michael Walkowiak, Leverkusen; Hans H. Schulz, Leichlingen, all of Fed. Rep. of Germany

[73] Assignee: Bayer Aktiengesellschaft, Fed. Rep. of Germany

[21] Appl. No.: 93,272

[22] Filed: Nov. 13, 1979

[30] Foreign Application Priority Data

Nov. 14, 1978 [DE] Fed. Rep. of Germany ....... 2849280

[51] Int. Cl.³ ...................... B32B 27/28; B32B 27/30; C08F 20/20
[52] U.S. Cl. .................................... 428/402; 526/301; 526/313; 526/323.1; 526/323.2
[58] Field of Search .................... 526/301, 313, 323.1, 526/323.2; 428/402

[56] References Cited

U.S. PATENT DOCUMENTS

| Re. 21,736 | 2/1940 | Kistler | 526/323.2 |
| 3,179,623 | 4/1965 | Bowen | 526/320 |
| 3,539,533 | 11/1970 | Lee et al. | 526/313 |
| 3,607,848 | 9/1971 | Stoy et al. | 526/323.1 |
| 3,635,889 | 1/1972 | Bowen | 526/313 |
| 3,730,947 | 5/1973 | Stoffey et al. | 526/313 |
| 3,825,518 | 7/1974 | Foster et al. | 526/301 |
| 3,835,090 | 9/1974 | Gander | 526/313 |
| 4,067,853 | 1/1978 | Schmitt et al. | 526/313 |

*Primary Examiner*—Harry Wong, Jr.
*Attorney, Agent, or Firm*—Connolly and Hutz

[57] ABSTRACT

Bead polymers having a mean bead diameter of from 10 to 200μ of one or more polymerized viscous methacrylates and/or dimethacrylates having a viscosity of from 0.5 to 500 Pa.s and, optionally, up to 20% by weight of one or more other vinyl monomers.

4 Claims, No Drawings

BEAD POLYMERS OF VISCOUS DIMETHACRYLATES

This invention relates to polymers of viscous dimethacrylates and, optionally, up to 20%, by weight, of other vinyl monomers in the form of beads having a mean diameter ($d_{50}$) of from 10 to 200μ.

Methyl methacrylate bead polymers of the type in question are used as a component of dental plastics, for example for the production of false teeth by the powder/liquid process according to German Pat. No. 737,058. They are obtained in known manner by suspension polymerisation ("bead polymerisation"). In bead polymerisation, the monomer is dispersed to the required particle size while stirring in water using a suitable dispersant and subsequently polymerised within the individual droplets by means of a monomer-soluble initiator.

The bead polymerisation of highly viscous substances presents particular difficulties because suspensions thereof show an increased tendency to coagulate. In general, it is only possible to obtain coarse beads, i.e. beads from one to a few millimeters in size, the shape of which is other than spherical (cf. German Pat. No. 755 028 and French Pat. No. 1,005,601).

The present invention relates to bead polymers having a mean bead diameter of from 10 to 200μ of polymerised viscous dimethacrylates and, optionally, up to 20%, by weight, of other vinyl monomers. These bead polymers are suitable for use as fillers in pasteform dental compositions.

Starting materials for the bead polymers according to the present invention are dimethacrylates corresponding to general formula (III) below. It is also possible to use mixtures of different dimethacrylates providing the viscosity of the mixture is from 0.5 to 500 Pa s, for example mixtures of the above-mentioned monomers and the methacrylic acid esters of ethylene glycol, di-, tri-, or tetra-ethylene glycol.

The viscous dimethacrylates or sufficiently viscous mixtures thereof may be used on their own as starting material, although they may contain up to 20%, by weight of other vinyl monomers which, in that case, are incorporated in the polymer, for example alkyl methacrylates, such as methyl methacrylate, alkyl acrylate, styrene, divinyl benzene or vinyl acetate.

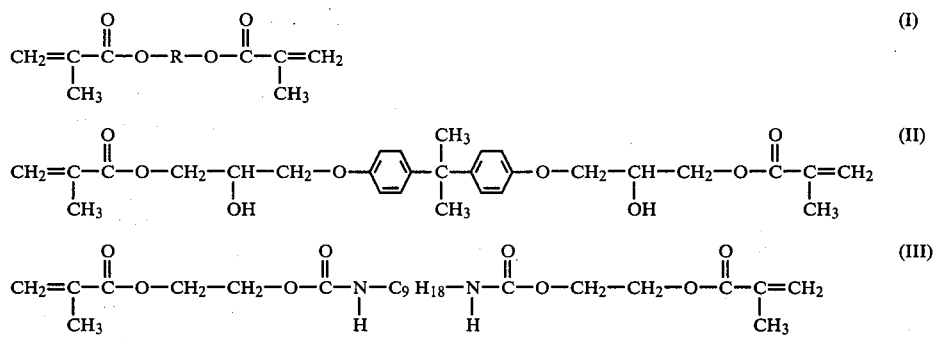

ing to general formula (I) below wherein R represents the residue of a diol; the dimethacrylates having a viscosity of from 0.5 to 500 Pa. s (as measured at 25° C. using a rotary viscosimeter). Particularly suitable starting materials are derivatives of bisphenol A, for example the reaction product of bisphenol A and glycidyl methacrylate corresponding to general formula (II) below known as bis-GMA. Equally suitable starting materials are urethane or urea dimethacrylates of the type obtained by reacting diisocyanates with hydroxyalkyl methacrylates or aminoalkyl methacrylates, for example the reaction product of 2,2,4-trimethyl hexamethylene diisocyanate and 2-hydroxyethyl methacrylate corresponding to general formula (III) below.

For producing the bead polymers according to the present invention, an initiator (for example benzoyl peroxide or cyclohexyl percarbonate) is added to the monomer or monomer mixture which is then suspended by high-speed stirring in an aqueous solution of a high molecular weight dispersant.

Particularly suitable dispersants are copolymers or vinyl alcohol/vinyl acetate obtained by partial hydrolysis or methacrylic acid/methyl methacrylate copolymers produced by copolymerisation.

The suspension obtained is polymerised with stirring by heating to the decomposition temperature of the initiator. The bead polymer may be obtained from the fully polymerised suspension in known manner by filtration, washing and drying.

The viscosities quoted in the following Examples were measured using a Haake rotary viscosimeter at 25° C.

EXAMPLE 1

Bead polymer of bis-GMA

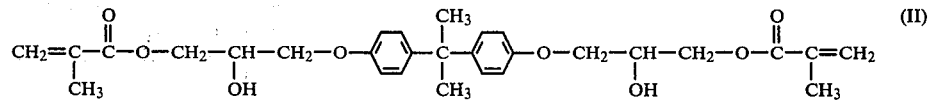

reaction vessel:

2-liter face-ground beaker equipped with a paddle stirrer, reflux condenser, internal thermometer, gas inlet and gas outlet pipe.

Mixture 1: monomer phase
200 g of bis-GMA
4 g of benzoyl peroxide the viscosity of the monomer phase amounts to 420,000 mPa.s.

Mixture 2: aqueous phase
550 ml of distilled water
250 ml of MAS MMA-dispersant solution [7.5% agueous solution of a copolymer of equal parts, by weight, of methacrylic acid methyl methacrylate, pH 6 (adjusted using NaOH), viscosity 3.6 Pa.s.]

Mixture 1 and Mixture 2 are introduced into the reaction vessel in the absence of air and stirred at 600 r.p.m. for 1 hour at 50° C. The suspension formed is heated with continued stirring to 80° C. and, when the reaction becomes exothermic, is cooled to such an extent that the reaction temperature is maintained below 90° C. After the reaction has abated, the mixture is maintained at a temperature of 85° C. for 2 hours. 1 liter of water is then added to the reaction mixture and the pH is adjusted to 3 by the addition of acetic acid. The bead polymer formed is separated off by filtration, repeatedly washed with distilled water and dried at 80° C.

Yield: 195 g of clear round beads
Mean bead diamter ($d_{50}$): 100μ.

EXAMPLE 2

Bead polymer of bis-GMA and triethylene glycol dimethacrylate.

Reaction vessel as in Example 1.
Mixture 1: monomer phase
188 g of bis-GMA
112 g of triethylene glycol dimethacrylate
3 g of benzoyl peroxide
The viscosity of the monomer phase amounts to 1200 mPa.s.
Mixture 2: aqueous phase
700 ml of distilled water
300 ml of MAS-MMA-dispersant solution as in Example 1.

Mixture 1 and mixture 2 are stirred at 600 r.p.m. for 30 minutes at room temperature to form a suspension.

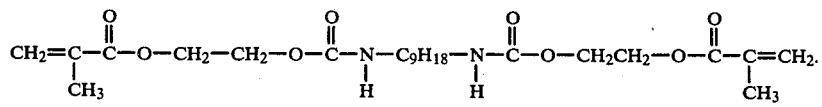

The suspension is polymerised to completion and worked-up in the same way as in Example 1.

Yield: 290 g of clear round beads
Mean bead diameter ($d_{50}$): 30μ.

EXAMPLE 3

Bead polymer of a urethane dimethacrylate.

Mixture 1: monomer phase
300 g of the reaction product of 2,2,4-trimethyl hexamethylene diisocyanate and 2-hydroxyethyl methacrylate
3 g of benzoyl peroxide.

The viscosity of the monomer phase amounts to 7500 mPa s.

The procedure is as in Example 2 using similar aqueous phase.

Yield: 276 g of round beads
Mean bead diameter ($d_{50}$): 70μ.

We claim:

1. A bead having a mean bead diameter of from 10 to 200 microns, said bead comprising
    (a) 100 to 80% by weight of polymerized viscous dimethacrylate of the formula

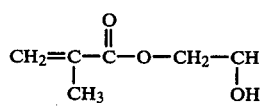

wherein R is the residue of a diol, said viscous dimethylacrylate having a viscosity of from 0.5 to 500 Pa.s. measured at 25° C. using a rotary viscosimeter, and
    (b) 0 to 20% by weight of at least one other copolymerized vinyl monomer.

2. The bead of claim 1 wherein the viscous dimethacrylate is bis-GMA of the formula

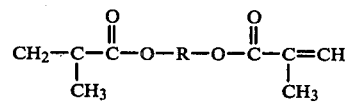

3. The bead of claim 1 wherein the viscous dimethacrylate is the reaction product of trimethylhexamethylene diisocyanate and 2-hydroxyethylmethacrylate of the formula

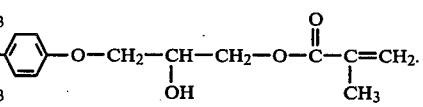

4. The bead of claim 1 wherein said other vinyl monomer is selected from the group consisting of alkyl methacrylates, alkyl acrylates, styrene, divinyl benzene and vinyl acetate.

* * * * *